US011131678B2

(12) United States Patent
Schneeweiss et al.

(10) Patent No.: US 11,131,678 B2
(45) Date of Patent: Sep. 28, 2021

(54) ANALYSIS OF ANTI-ERYTHROCYTE ANTIBODY IN THE PRESENCE OF ANTIBODY DIRECTED AGAINST A SURFACE-BOUND ERYTHROCYTE ANTIGEN

(71) Applicant: IMUSYN GMBH & CO. KG, Hannover (DE)

(72) Inventors: Clemens Schneeweiss, Hannover (DE); Daniela Grüger, Ilsede (DE)

(73) Assignee: IMUSYN GMBH & CO. KG, Hannover (DE)

( * ) Notice: Subject to any disclaimer, the term of this patent is extended or adjusted under 35 U.S.C. 154(b) by 62 days.

(21) Appl. No.: 16/463,278

(22) PCT Filed: Nov. 30, 2017

(86) PCT No.: PCT/EP2017/080926
§ 371 (c)(1),
(2) Date: May 22, 2019

(87) PCT Pub. No.: WO2018/100036
PCT Pub. Date: Jun. 7, 2018

(65) Prior Publication Data
US 2019/0310268 A1    Oct. 10, 2019

(30) Foreign Application Priority Data

Dec. 1, 2016 (EP) .................................. 16201819
Jan. 9, 2017 (EP) .................................. 17150738

(51) Int. Cl.
| | | |
|---|---|---|
| *G01N 33/80* | (2006.01) | |
| *G01N 33/555* | (2006.01) | |
| *G01N 33/541* | (2006.01) | |
| *G01N 33/563* | (2006.01) | |
| *G01N 33/68* | (2006.01) | |

(52) U.S. Cl.
CPC .......... *G01N 33/80* (2013.01); *G01N 33/541* (2013.01); *G01N 33/555* (2013.01); *G01N 33/563* (2013.01); *G01N 33/6854* (2013.01); *G01N 2333/70596* (2013.01); *G01N 2333/91148* (2013.01)

(58) Field of Classification Search
CPC .... G01N 33/80; G01N 33/541; G01N 33/555; G01N 33/563; G01N 33/6854; G01N 2333/70596
See application file for complete search history.

(56) References Cited

U.S. PATENT DOCUMENTS

2012/0202225 A1    8/2012    Knutson et al.

FOREIGN PATENT DOCUMENTS

| WO | 2006099875 A1 | 9/2006 |
| WO | 2008122793 A1 | 10/2008 |

OTHER PUBLICATIONS

Chapuy et al. Resolving the daratumumab interference with blood compatibility testing. Transfusion 55: 1545-1554 (Jun. 2015)—IDS.*
Chapuy, Claudia et al., "Resolving the daratumumab interference with blood compatibility testing", Transfusion, 55: 1545-1554, Jun. 2015.
Seltsam, Axel et al., "Recombinant blood group proteins facilitate the detection of alloantibodies to high-prevalence antigens and reveal underlying antibodies: results of an international study". Transfusion, 54: 1823-1830, Jul. 2014.
De Vega, Moreno, International Search Report for Application No. PCT/EP2017/080926, dated Jan. 12, 2018.

* cited by examiner

*Primary Examiner* — Gailene Gabel
(74) *Attorney, Agent, or Firm* — Greer, Burns & Crain, Ltd.; Steven P. Fallon

(57) ABSTRACT

An analytical process for detecting antibody in human blood serum, which antibody is directed against blood group antigen, wherein the serum contains an additional antibody directed against a surface antigen, by contacting the serum to be analysed with blood cell membranes, which naturally bear surface blood group antigens, followed by detection of agglutination which indicated the presence of antibody directed against at least one surface antigen of the blood cell membranes. The agglutination reaction caused by the additional antibody is prevented, allowing the detection of anti-blood group antibody.

13 Claims, 3 Drawing Sheets

Fig. 2

Figure 1:
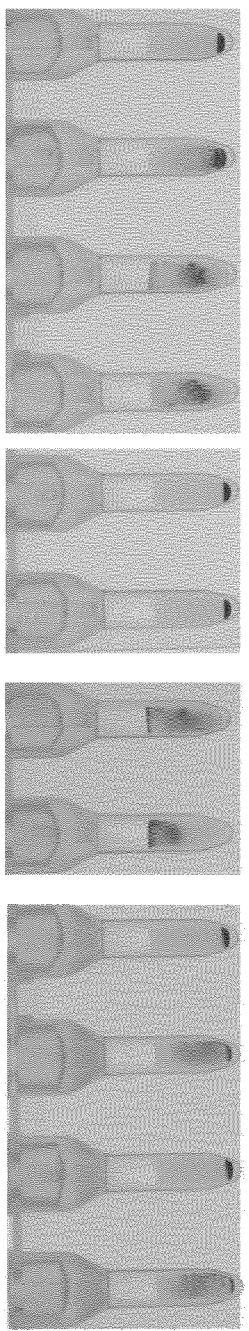

| pre-incubation | serum | anti-Kell | | | | DARA | | | | anti-Fy(a) | | | |
|---|---|---|---|---|---|---|---|---|---|---|---|---|---|
| | Well No. | 1 | 2 | 3 | 4 | 5 | 6 | 7 | 8 | 9 | 10 | 11 | 12 |
| | Cell No. | 2 | 2 | 4 | 4 | 2 | 2 | 4 | 4 | 2 | 2 | 4 | 4 |
| TBS | | + | - | + | - | + | - | + | - | + | - | + | - |
| DARA-F(ab)₂ | | - | + | - | + | - | + | - | + | - | + | - | + |

| pre-incubation | serum | DARA + anti-Kell | | | | DARA + anti-Fy(a) | | | |
|---|---|---|---|---|---|---|---|---|---|
| | Well No. | 13 | 14 | 15 | 16 | 17 | 18 | 19 | 20 |
| | Cell No. | 2 | 2 | 4 | 4 | 2 | 2 | 4 | 4 |
| TBS | | + | - | + | - | + | - | + | - |
| DARA-F(ab)₂ | | - | + | - | + | - | + | - | + |

ANALYSIS OF ANTI-ERYTHROCYTE ANTIBODY IN THE PRESENCE OF ANTIBODY DIRECTED AGAINST A SURFACE-BOUND ERYTHROCYTE ANTIGEN

The present invention relates to an analytical process for detecting antibody in human blood serum, which antibody is directed against blood group antigen. In the process, the serum to be analysed is contacted with blood cell membranes, which naturally bear surface blood group antigens, followed by detection of agglutination which indicated the presence of antibody directed against at least one surface antigen of the blood cell membranes. Optionally, the process can comprise the step of adding a reagent or using conditions promoting agglutination, e.g. an anti-human antibody, albumin, polyethylene glycol (PEG) and/or proteolytic enzymes, and/or contacting the serum with the blood cell membranes in low ionic strength solution (LISS).

STATE OF THE ART

WO 2006/099875 describes a therapeutic antibody directed against CD38 for the treatment of multiple myeloma.

Chapuy et al., Transfusion Vol. 55, 1545-1554 (2015) describe that an anti-CD38 antibody termed Daratumumab (DARA), which is used for treatment of multiple myeloma, causes agglutination of red blood cells (RBC) in a serologic assay for detecting anti-blood group antibody in serum. The agglutination of RBC by DARA could be abolished by treatment of RBC with DTT or with trypsin, resulting in the denaturation or removal of CD38, or by addition of anti-DARA idiotype antibody, or by addition of soluble CD38.

It is known as the Coombs test to detect in human serum antibody directed against blood group antigen by contacting the serum with red blood cells in the presence of anti-human antibody. The anti-human antibody serves to cross-link antibody directed against cell-surface bound antigen, resulting in an optically detectable agglutination of the red blood cells.

OBJECT OF THE INVENTION

It is an object of the invention to provide an alternative analytical process for detecting anti-blood group antibody in a serum. Preferably, the serum contains an antibody specific for a surface antigen of a blood cell which surface antigen is no blood group antigen, especially a serum that contains an antibody specific for a surface antigen of an RBC, which antibody was introduced into the serum artificially, e.g. introduced into the serum by infusion into a patient containing the antibody as a medicament.

DESCRIPTION OF THE INVENTION

The invention achieves the object by an analytical process according to the claims, especially by an analytical process for detecting an antibody directed against a blood group antigen by contacting the blood serum to be analysed with blood cell membranes, followed by detecting the binding of antibody from the serum to the blood cell membranes. The process is characterized by the step of adding at least one binding peptide which is specific for a first surface antigen of the blood cell membranes to the blood cell membranes prior to the step of contacting the blood cell membranes with the serum. The binding peptide has no human Fc region. The prior addition of the binding peptide to the blood cell membranes results in masking the first antigen of the blood cell membranes and as a consequence prevents the binding of an antibody from the serum to the first antigen, which serum is contacted subsequently with the blood cell membranes. In this process, the detection of the binding of serum antibody to blood cell membranes by observing agglutination of blood cell membranes and for the alternative observation of binding of an added secondary labelled antibody directed against the Fc region of serum antibody, it was shown that the detection for antibody present in the serum which is directed against the first antigen revealed no antibody bound to the first antigen. This shows that the binding peptide which is specific for a first surface antigen of the blood cell membranes when bound to the blood cell membranes prevents the detection of antibody from the serum directed against the first antigen and allows the detection of other antibodies of the serum which subsequently bind to other antigens of the blood cell membranes.

The binding peptide is characterized by lacking a human Fc region, which e.g. in IgG type antibodies consists of two chains, each of which contains a $C_H2$ and a $C_H3$ domain. The binding peptide forms a paratope with high specificity for the first surface antigen of the blood cell, which binding peptide can be a natural or synthetic peptide, in one or more associated polypeptide chains. Examples of binding peptides include proteins having at least one, preferably two, regions forming at least one paratope specifically binding to the first antigen, e.g. antibody fragments having no Fc region, $F(ab)_2$ fragments, Fab fragments, single-chain variable domain fragments (scFv), minibodies, microbodies, nanobodies, diabodies, and antibodies having a non-human Fc region.

Generally, an antibody of the serum herein is generally also referred to as serum antibody. A serum antibody which is specific for the first antigen will bind to the blood cell membranes which bear the first antigen as one of their surface antigens in the absence of prior contacting the blood cell membranes with a binding peptide which is specific for the first antigen.

Generally, the blood group antigens of the blood cell membranes are predetermined, allowing the deduction of the specificities of antibodies of the serum to a certain degree. The blood cell membranes can be erythrocytes, membrane vesicles, optionally containing a colour, e.g. haemoglobin, or membrane fragments bound to a solid carrier, which solid carrier preferably is labelled by an optically readable graphic pattern or a dye, or by arrangement of the solid carrier in a position known to a reading device. In these embodiments, the information on the predetermined blood group antigens of the blood cell membranes is associated with the label associated with the solid carrier in order to subsequently allocate via this label the information on the predetermined blood group antigens to the measured presence or absence of bound serum antibody. Solid carriers which are individually labelled for each species of blood cell membrane can be used in combination of at least two solid carriers, each having immobilized one species of blood cell membranes and an individual label attached to the solid carrier.

The process of the invention has the advantage that the serum to be analysed is not affected directly, because the blood cell membranes are contacted with the binding peptide which is specific for the first antigen prior to contacting the blood cell membranes with the serum. Accordingly, the reaction of serum antibody with the blood cell membranes is not affected by the process, except for the reaction of a serum antibody which is specific for the first surface antigen.

The first surface antigen can be an antigen which is no blood group antigen, e.g. a cell surface protein present in all humans. In this embodiment, antibodies of the serum can bind to all their specific surface antigens, with the exception of the binding of a serum antibody that is specific for the first antigen to the first surface antigen. Accordingly, a serum antibody which is specific for the first surface antigen present on all types blood cell membranes, each type containing a different set of blood group antigens, is prevented from binding to all types of blood cell membranes due to the prior contacting of the blood cell membranes with the binding peptide specific for the first surface antigen, and is prevented from causing a non-specific detection of serum antibody on all the types of blood cell membranes bearing the first antigen.

Preferably, the serum contains an antibody which was administered to the respective patient, e.g. the serum originates from a patient who has been administered with an antibody, especially a therapeutic antibody, which antibody is directed against, e.g. has affinity for, a first antigen which is present also on blood cell membranes. In this embodiment, the binding peptide is directed against the same first antigen as the administered antibody. The binding peptide can have the same paratope regions as the therapeutic antibody that was administered. The binding peptide in this embodiment is e.g. obtainable by separating, e.g. by protease digestion, the Fc region from the therapeutic antibody, resulting in a F(ab)$_2$ fragment or Fab fragment. Examples for such therapeutic antibodies are an anti-CD38 antibody e.g. available under the name Daratumumab and DARZALEX, or an anti-CD44 antibody that has recently entered phase I clinical trials for the treatment of CD44 expressing solid tumours.

Alternatively or additionally, the first antigen is or comprises a blood group antigen, and the binding peptide is specific for the same blood group antigen. Also in this embodiment, the binding peptide, or a combination of binding peptides, are obtainable by separating their Fc region from an antibody, e.g. from an IgG specific for the blood group antigen.

Blood group antigens preferably comprise or consist of the antigens belonging to the blood group systems ABO, MNS, P, Rh, Lutheran, Kell, Lewis, Duffy, Kidd, Diego, Yt, Xg, Scianna, Dombrock, Colton, Landsteiner-Wiener, Chido/Rogers, H, Kx, Gerbich, Cromer, Knops, Indian, Ok, Raph, John Milton Hagen, I, Globoside, Gill, and Rh-associated glycoprotein, or belonging to the blood group collections Cost, li, Er, 209, 210, and Vel, or belonging to the low and high incidence antigens of the 700 and the 901 series, according to the nomenclature of the International Society for Blood Transfusion, Committee on Terminology for Red Cell Surface Antigens.

Generally, the process for detecting antibody specific for blood group antigen in serum comprises or consists of the steps of
a) providing at least one type of blood cell membranes, the blood group antigens of which are predetermined,
b) prior to step c), adding to the blood cell membranes at least one binding peptide which has no human Fc region, which binding peptide has specificity for a first surface antigen of the blood cell membranes, to provide blood cell membranes in which their first surface antigen is bound by the binding peptide,
c) contacting the serum with the blood cell membranes in which their first surface antigen is bound by the binding peptide, and
d) detecting antibody bound to the blood cell membranes in which their first surface antigen is bound by the binding peptide.

Detecting antibody, which is antibody from the serum, bound to the blood cell membranes can be by determining agglutination, preferably with addition of a reagent promoting agglutination, preferably an anti-human antibody. Determination of agglutination can be by layering the reaction mixture on top of a bed of gel particles and observing movement of the blood cell membranes through the bed of gel particles, preferably after applying increased gravity by centrifugation for movement of the blood cell membranes through the bed of gel particles. In this embodiment, at least two species of blood cell membranes, each species bearing a different combination of blood group antigens, are contained in separate reactions, which preferably are treated in parallel by the process steps.

In the alternative, the blood cell membranes can be connected to a solid carrier and detection of antibody is by measuring the presence or absence of a secondary antibody, e.g. a labelled anti-human antibody, on the solid carrier.

In step b), after adding the at least one binding peptide to the blood cell membranes, a washing step can be performed. As binding peptide which is not bound to blood cell membranes does not influence the binding of serum antibody to the blood cell membranes, step b) can be performed without removing unbound binding peptide from the blood cell membranes, e.g. without a subsequent washing step.

Figure 3:
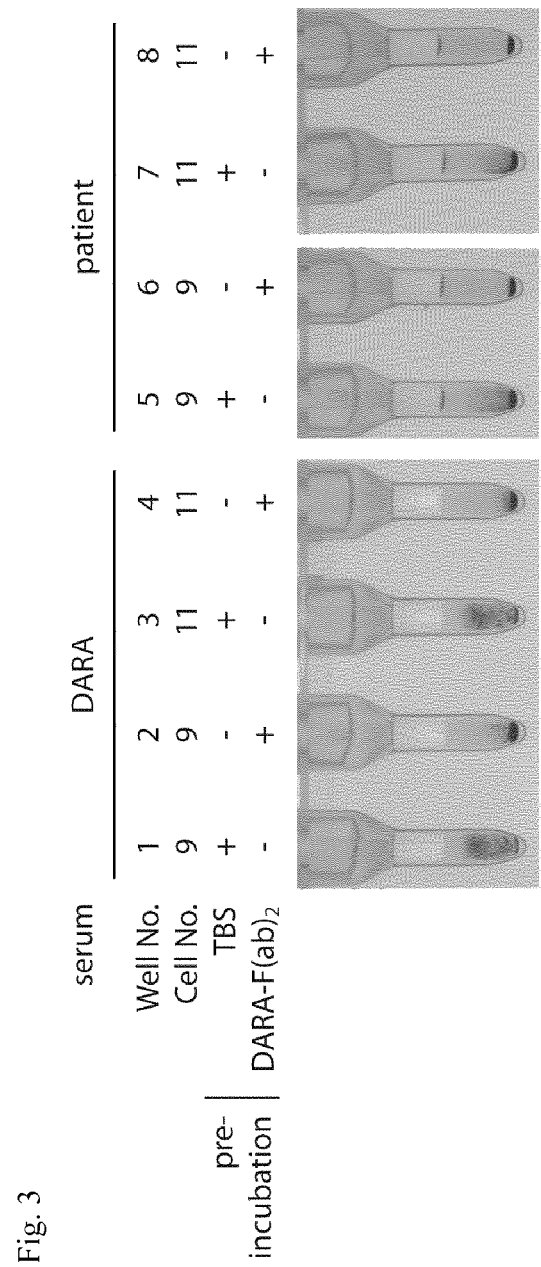

The invention is now described in greater detail by way of examples with reference to the figures, which show in FIG. 1 results of a Coombs agglutination test using gel cards for s positive and negative erythrocytes with anti-s serum, FIG. 2 results of a Coombs agglutination test using gel cards for Kell and Fy(a) with anti-Kell and anti-Fy(a) serum, and FIG. 3 results of a Coombs agglutination test on a patient serum using gel cards.

In the examples, agglutination was determined to detect binding of antibody to the blood cell membranes, e.g. to detect binding of anti-blood group antibody of a serum to blood cell membranes bearing the specific blood group antigen.

Example 1: Analysis of Anti-Blood Group Antibodies in Serum

As an example for an antibody directed against a first antigen present on all blood cell membranes, the therapeutic anti-CD38 antibody Daratumumab (DARA) was used in a 0.9% NaCl solution as a comparison (DARA only) or spiked into the serum prior to contacting with the blood cell membranes. As blood cell membranes, 60 μL erythrocytes were used in an agglutination assay using gel cards containing anti-human antibody (Coombs). The binding protein was the F(ab)$_2$ fragment generated from Daratumumab by pepsin digestion in 100 mM citric acid buffer for 60 min at 37° C. in a 40-fold molar excess of pepsin over Daratumumab. The digestion was stopped by adding Tris-buffered saline (TBS, pH 8.0). This binding protein is designated DARA-F(ab)$_2$. 100 μL of 0.3 μg/μL DARA-F(ab)$_2$ was added to 300 μL erythrocytes under shaking at room temperature as a pre-incubation, for comparative reactions, 100 μL TBS was used instead. For the agglutination reaction, 60 μL of these erythrocytes were incubated with 25 μL serum for 15 min at 37° C., layered onto the gel bed in the gel card wells, containing an anti-human antibody, and centrifuged according to the manufacturer's instructions.

The erythrocytes were predetermined to be s positive for Cell-7 and s negative for Cell-11. The serum was human serum (obtained from Biolith, 1:2 dilution) known to contain anti-s antibody.

FIG. 1 shows the gel cards after centrifugation, containing the following reactions:

| Well No. | Cell | serum | Reaction |
| --- | --- | --- | --- |
| 1 | Cell-7 pre-incubated with TBS | DARA only | agglutination |
| 2 | Cell-7 pre-incubated with DARA-F(ab)$_2$ | DARA only | no agglutination |
| 3 | Cell-11 pre-incubated with TBS | DARA only | agglutination |
| 4 | Cell-11 pre-incubated with DARA-F(ab)$_2$ | DARA only | no agglutination |
| 5 | Cell-7 pre-incubated with TBS | anti-s serum only | agglutination |
| 6 | Cell-7 pre-incubated with DARA-F(ab)$_2$ | anti-s serum only | agglutination |
| 7 | Cell-11 pre-incubated with TBS | anti-s serum only | no agglutination |
| 8 | Cell-11 pre-incubated with DARA-F(ab)$_2$ | anti-s serum only | no agglutination |
| 9 | Cell-7 pre-incubated with TBS | DARA + anti-s serum | agglutination |
| 10 | Cell-7 pre-incubated with DARA-F(ab)$_2$ | DARA + anti-s serum | agglutination |
| 11 | Cell-11 pre-incubated with TBS | DARA + anti-s serum | agglutination |
| 12 | Cell-11 pre-incubated with DARA-F(ab)$_2$ | DARA + anti-s serum | no agglutination |

Wells 1 to 4 show comparative reactions containing no serum with anti-blood group antibody, but anti-CD38 antibody DARA and anti-human antibody (Coombs) only. These results show that the anti-CD38 antibody DARA leads to an agglutination of the untreated erythrocytes and that pre-treatment of erythrocytes by adding DARA-F(ab)$_2$ results in abolishment of the agglutination.

Wells 5 to 8 show reactions containing only serum with anti-blood group antibody, but no anti-CD38 antibody DARA. These results show that the agglutination of s-positive Cell-7 by anti-s serum and the non-agglutination of s-negative Cell-11 with anti-s serum are not affected by the pre-incubation of the erythrocytes with the DARA-F(ab)$_2$ binding peptide.

Well 9 shows that in the presence of the anti-s serum, without pre-treatment of erythrocytes by a binding peptide, an antibody (DARA) directed against a non-blood group antigen (CD38), or an anti-blood group antibody, currently anti-s, results in agglutination.

Well 10 shows that adding a binding peptide that has no human Fc-region (DARA-F(ab)$_2$) and which is directed against a first antigen, exemplified by CD38, does not influence the binding of the anti-s serum antibody to the erythrocytes.

Well 11 shows that in the presence of the anti-s serum, without pre-treatment of erythrocytes by a binding peptide, an antibody (DARA) directed against a non-blood group antigen (CD38) in a serum (anti-s) results in agglutination also for cells which do not bear the blood group antigen s.

Well 12 shows that adding a binding peptide that has no human Fc-region (DARA-F(ab)$_2$) and which is directed against a first antigen, exemplified by CD38, does not influence the non-binding of the anti-s serum antibody to the erythrocytes which do not bear the s antigen.

Accordingly, the addition of a binding peptide which does not have a human Fc-region and which is specific for a first antigen present on blood cell membranes results in the specific masking of the first antigen on the blood cell membranes without affecting the binding or non-binding, respectively, of other antibodies of a serum.

Example 2: Analysis of Anti-Blood Group Antibodies in Serum

As described in Example 1, the therapeutic anti-CD38 antibody DARA was used as an antibody directed against the exemplary first antigen CD38, and DARA-F(ab)$_2$ was used as the binding peptide specific for the first antigen. The blood cell membranes were represented by erythrocytes Cell-2 (Kell positive, Fy(a) negative) and Cell-4 (Kell negative, Fy(a) positive) using human anti-Kell serum (obtained from Grifols, 1:2 dilution) or human anti-Fy(a) serum (obtained from Biolith, 1:2 dilution). Binding of serum antibody to the erythrocytes was detected by the agglutination reaction according to Example 1.

FIG. 2 shows the gel cards after centrifugation, containing the following reactions:

| well No. | cell | serum | reaction |
| --- | --- | --- | --- |
| 1 | Cell-2 pre-incubated with TBS | anti-Kell serum only | agglutination |
| 2 | Cell-2 pre-incubated with DARA-F(ab)$_2$ | anti-Kell serum only | agglutination |
| 3 | Cell-4 pre-incubated with TBS | anti-Kell serum only | no agglutination |
| 4 | Cell-4 pre-incubated with DARA-F(ab)$_2$ | anti-Kell serum only | no agglutination |
| 5 | Cell-2 pre-incubated with TBS | DARA only | agglutination |
| 6 | Cell-2 pre-incubated with DARA-F(ab)$_2$ | DARA only | no agglutination |
| 7 | Cell-4 pre-incubated with TBS | DARA only | agglutination |
| 8 | Cell-4 pre-incubated with DARA-F(ab)$_2$ | DARA only | no agglutination |
| 9 | Cell-2 pre-incubated with TBS | anti-Fy(a) serum only | no agglutination |
| 10 | Cell-2 pre-incubated with DARA-F(ab)$_2$ | anti-Fy(a) serum only | no agglutination |
| 11 | Cell-4 pre-incubated with TBS | anti-Fy(a) serum only | agglutination |
| 12 | Cell-4 pre-incubated with DARA-F(ab)$_2$ | anti-Fy(a) serum only | agglutination |
| 13 | Cell-2 pre-incubated with TBS | DARA + anti-Kell serum | agglutination |
| 14 | Cell-2 pre-incubated with DARA-F(ab)$_2$ | DARA + anti-Kell serum | agglutination |
| 15 | Cell-4 pre-incubated with TBS | DARA + anti-Kell serum | agglutination |
| 16 | Cell-4 pre-incubated with DARA-F(ab)$_2$ | DARA + anti-Kell serum | no agglutination |
| 17 | Cell-2 pre-incubated with TBS | DARA + anti-Fy(a) serum | agglutination |
| 18 | Cell-2 pre-incubated with DARA-F(ab)$_2$ | DARA + anti-Fy(a) serum | no agglutination |
| 19 | Cell-4 pre-incubated with TBS | DARA + anti-Fy(a) serum | agglutination |
| 20 | Cell-4 pre-incubated with DARA-F(ab)$_2$ | DARA + anti-Fy(a) serum | agglutination |

Wells 1 to 4 show that the anti-Kell serum agglutinates only the erythrocytes depending on the presence of the specific blood group antigen Kell, independent of the addition of the binding peptide DARA-F(ab)$_2$ prior to contacting the erythrocytes with the human serum.

Wells 9 to 12 show that the anti-Fy(a) serum agglutinates only the erythrocytes depending on the presence of the specific blood group antigen Fy(a), independent of the addition of the binding peptide DARA-F(ab)$_2$ prior to contacting the erythrocytes with the human serum.

This shows also for blood group antigens Kell and Fy(a) that the binding of the respective specific antibodies from serum is not influenced by the binding of the binding peptide to the blood cell membranes prior to their contact with the serum to be analysed.

Wells 5 to 8 show that the antibody directed to a first antigen which is present on the blood cell membranes, results in binding of the antibody to the cells, and that this binding is prevented by addition of a binding peptide specific for the first antigen prior to contact with the antibody, and also that the cross-linking activity of anti-human antibody (Coombs) as used in the gel-card assay is not present with the binding peptide which has no human Fc-region. The further wells show that the cross-linking activity of anti-human antibody (Coombs) for anti-blood group antibodies of the serum that bind to the blood cell membranes is not influenced by the added binding peptide of the invention.

Wells 13, 15, 17, and 19 show that the erythrocytes without pre-incubation with a binding peptide directed against a first antigen are bound by an antibody directed against the first antigen, resulting in agglutination, independent from the anti-blood group specificity of the serum contacted with the erythrocytes. Wells 14, 16, 18, and 20 show that the addition of the binding peptide that lacks a human Fc-region and has specificity for a first antigen prevents binding of an antibody present in the serum, which antibody is directed against the first antigen, and show that the binding of anti-blood group antibodies of the serum to the blood cell membranes is not affected by the prior addition of the binding peptide which is specific for the first antigen, which is not a blood group antigen recognized by the anti-blood group antibodies of the serum.

Example 3: Inhibition of DARA in Patient Serum

Corresponding to Example 1, the therapeutic anti-CD38 antibody DARA was contained in the serum as an antibody directed against the exemplary first antigen CD38, which serum was obtained from a patient treated with the therapeutic anti-CD38 antibody DARA. DARA-F(ab)$_2$ was used as the binding peptide specific for the first antigen. The blood cell membranes were represented by erythrocytes Cell-9 and Cell-11. Binding of serum antibody to the erythrocytes was detected by the agglutination reaction according to Example 1.

FIG. 3 shows the gel cards after centrifugation, containing the following reactions:

| Well No. | Cell | serum | reaction |
| --- | --- | --- | --- |
| 1 | Cell-9 pre-incubated with TBS | DARA only | agglutination |
| 2 | Cell-9 pre-incubated with DARA-F(ab)$_2$ | DARA only | no agglutination |
| 3 | Cell-11 pre-incubated with TBS | DARA only | agglutination |
| 4 | Cell-11 pre-incubated with DARA-F(ab)$_2$ | DARA only | no agglutination |
| 5 | Cell-9 pre-incubated with TBS | Patient serum | agglutination |
| 6 | Cell-9 pre-incubated with DARA-F(ab)$_2$ | Patient serum | no agglutination |
| 7 | Cell-11 pre-incubated with TBS | Patient serum | agglutination |
| 8 | Cell-11 pre-incubated with DARA-F(ab)$_2$ | Patient serum | no agglutination |

Cell-9 carries the typed antigens Rhc, Rhe, Cellano, Kp(b), Kp(a), Fy(a), Fy(b), Jk(b), Le(b), P1, M, S, s, and Lu(b). Cell-11 carries the typed antigens Rhc, Rhe, Cellano, Kp(b), Fy(b), Jk(a), Le(b), P1, N, S, Lu(b), Xg(a), Bga(w)

Wells 1 to 4 show comparative reactions containing no serum with anti-blood group antibody, but anti-CD38 antibody DARA and anti-human antibody (Coombs) only. These results show that the anti-CD38 antibody DARA leads to an agglutination of all the untreated erythrocytes and that pre-treatment of erythrocytes by adding DARA-F(ab)$_2$ results in abolishment of this agglutination.

Wells 5 to 8 show comparative reactions containing patient serum with unknown or no anti-blood group antibodies, but anti-CD38 antibody due to treatment with DARA. These results show that the agglutination of the untreated erythrocytes due to the anti-CD38 antibody DARA in a patient serum can be abolished by pre-treatment of erythrocytes by adding DARA-F(ab)$_2$. The reactions of wells 5 to 8 show that this patient is negative for antibodies against the antigens on Cell-9 and Cell-11.

The results demonstrate that pre-treating the blood cell membranes, represented by erythrocytes, with a binding peptide specific for the same first antigen (CD38) of the blood cell membranes, which binding peptide contains no human Fc-region, rendered the serum antibody inactive that is specific for the first antigen. For the determination of blood group antibodies, the pre-incubation of the blood cell membranes with such a binding peptide turned a non-conclusive result into a conclusive result, as the all-positive agglutination reactions were turned into reactions specifically showing the effect of other serum antibodies.

The invention claimed is:

1. Analytical process for detecting antibody specific for a blood group antigen in blood serum, comprising contacting the serum with blood cell membranes bearing surface antigens, and prior to contacting the serum with blood cell membranes, adding at least one binding peptide specifically binding to a first surface antigen of the blood cell membranes to the blood cell membranes, which binding peptide has no human Fc region; wherein the blood cell membranes are red blood cells or membrane fragments of red blood cells.

2. The analytical process according to claim 1 wherein the first antigen is not a blood group antigen.

3. The analytical process according to claim 2, wherein prior to contacting the serum with blood cell membranes, the method further comprises adding at least one binding peptide specifically binding to a blood group antigen to the blood cell membranes, which binding peptide has no human Fc region.

4. The analytical process according to claim 1 wherein the first antigen is a blood group antigen.

5. The analytical process according to claim 1, wherein the binding peptide is selected from the group consisting of F(ab)$_2$ fragments, Fab fragments, single-chain variable domain fragments (scFv), minibodies, diabodies, antibodies having a non-human Fc region, and proteins having at least one region forming at least one paratope specifically binding to the first antigen.

6. The analytical process according to claim 1, wherein the serum is contacted with the blood cell membranes in the presence of anti-human antibody.

7. The analytical process according to claim 1, wherein the blood cell membranes are bound to a synthetic carrier and wherein the antibody specific for a blood group antigen from blood serum is bound to the blood cell membranes and wherein the analytical process further comprises detecting said antibody by adding a labelled anti-human antibody.

8. The analytical process according to claim 1, further comprising detecting agglutination.

9. The analytical process according to claim 1, wherein the first antigen is CD38 and the antibody which is directed against a surface antigen of a blood cell is specific for CD38.

10. The analytical process according to claim 1, wherein the binding peptide is labelled with a detectable marker.

11. The analytical process according claim 1, wherein the serum originates from a patient who has been administered with an antibody directed against the first antigen.

12. The analytical process according to claim 1, wherein the binding peptide has the same paratope regions as an antibody having the same specificity as the binding peptide, which antibody is contained in the serum.

13. The analytical process according to claim 1, wherein the binding peptide is derived from the antibody having the same specificity.

\* \* \* \* \*